(12) United States Patent
Ghandour et al.

(10) Patent No.: US 6,516,276 B1
(45) Date of Patent: Feb. 4, 2003

(54) METHOD AND APPARATUS FOR ANALYSIS OF DATA FROM BIOMOLECULAR ARRAYS

(75) Inventors: Ghassan Ghandour, Atherton, CA (US); Richard Glynne, Palo Alto, CA (US)

(73) Assignee: EOS Biotechnology, Inc., South San Francisco, CA (US)

(*) Notice: Subject to any disclaimer, the term of this patent is extended or adjusted under 35 U.S.C. 154(b) by 0 days.

(21) Appl. No.: 09/336,506

(22) Filed: Jun. 18, 1999

(51) Int. Cl.[7] ........................... G01N 31/00; G06F 19/00
(52) U.S. Cl. ............................................. 702/27; 435/6
(58) Field of Search ............................. 702/23, 22, 20, 702/19, 27, 30, 85, 181, 104; 435/4, 5, 6

(56) References Cited

U.S. PATENT DOCUMENTS

| | | | |
|---|---|---|---|
| 4,981,783 A | 1/1991 | Augenlicht | 435/6 |
| 5,733,729 A | 3/1998 | Lipshutz et al. | 435/6 |
| 5,795,716 A | 8/1998 | Chee et al. | 435/6 |
| 5,863,736 A * | 1/1999 | Haaland | 435/6 |
| 5,873,052 A | 2/1999 | Sharaf | 702/20 |
| 5,925,525 A | 7/1999 | Fodor et al. | 435/6 |
| 5,974,164 A | 10/1999 | Chee | 382/129 |
| 6,228,575 B1 * | 5/2001 | Gingeras et al. | 435/6 |
| 6,228,593 B1 * | 5/2001 | Lipshutz et al. | 435/6 |
| 6,245,517 B1 * | 6/2001 | Chen et al. | 435/6 |
| 6,251,588 B1 * | 6/2001 | Shannon et al. | 435/6 |
| 6,270,961 B1 * | 8/2001 | Drmanac | 435/6 |
| 6,309,824 B1 * | 10/2001 | Drmanac | 435/6 |
| 6,355,419 B1 * | 3/2002 | Alfenito | 435/6 |

FOREIGN PATENT DOCUMENTS

| WO | WO 97/27317 | 7/1997 |
|---|---|---|
| WO | WO 99/54724 | 10/1999 |

OTHER PUBLICATIONS

Yidong Cheng, et al., *Ratio–Based Decisions and the Quantitative Analysis of cDNA Microarray Images*, Journal of Biomedical Optics, vol. 2, No. 4, Oct. 1997.

David J. Duggan, et al., *Expression Profiling Using cDNA Microarrays*, Nature Genetics Supplement, vol. 21, Jan. 1999.

David J. Lockhart, et al., *Expression Monitoring by Hybridization to High–DensityOligonucleotice Arrays*, Bio/Technology, vol. 14, No. 13, Dec. 1, 1996.

Eric Perret, et al., *Improved Differential Screening Approach to Analyse Transcriptional Variations in Organized cDNA Libraries*, Gene (an international journal on genes and genomes), vol. 208, pp. 103–115, 1998.

"GeneChip Expression Analysis" Affymetrix, Inc., 4 pgs.

"GeneChip Expression Analysis Product Line", Affymetrix, Inc., 2 pgs.

Haberl, "Large–Scale Gene Expression Data Analysis and Quality Control,", published in "In Silico Biology Data Acquistion and Model Development," Cambridge Health Institute, Jun. 8–10, 1999, San Francisco, CA, 11 pgs.

* cited by examiner

Primary Examiner—John S. Hilten
Assistant Examiner—Demetrius Pretlow
(74) Attorney, Agent, or Firm—Fish & Richardson P.C.

(57) ABSTRACT

Computer programs and computer-implemented methods are disclosed for extracting, analyzing and comparing data from biomolecular binding experiments. The invention receives a set of values corresponding to the interaction of one or more target samples with probes on one or more arrays of biomolecular probes, and uses the values to generate one or more probability values indicating the probability that a molecular species complementary to the probe set is not present in the target samples, or is present at levels greater than or less than one or more reference levels. The probability values are generated by comparing the values for individual probes in a probe set with values for a calibration set, which may include a null set, spiked probe sets, or housekeeping probe sets. Normalized experimental values are generated for sets of probes on the arrays using statistical methods. Data is output in the form of data files including normalized experimental values and probability values for probe sets in the arrays.

36 Claims, 8 Drawing Sheets

METHOD AND APPARATUS FOR ANALYSIS OF DATA FROM BIOMOLECULAR ARRAYS

BACKGROUND OF THE INVENTION

The present invention relates to methods and apparatus for analyzing data extracted from biomolecular arrays.

Devices and methods for generating and analyzing arrays of biomolecules such as nucleic acids are known. Using such methods, nucleic acid probes are fabricated or "spotted" at an array of known locations on a substrate. A target sample containing one or more unknown fluorescence-labeled nucleic acids is then introduced onto the substrate and a scanner observes fluorescence resulting from binding or hybridization of the target with probes on the substrate. If the target sample includes RNA sequences taken from an organism or complementary DNA sequences produced from such RNA sequences, such experiments can be used to identify genes expressed in the organism.

Improved methods are needed to reliably evaluate the information resulting from use of these techniques.

SUMMARY OF THE INVENTION

The invention features computer-implemented methods and apparatus, including computer program products, operable for extracting, analyzing and comparing molecular affinity data from experiments.

In general, in one aspect, the invention features a method of analyzing an experiment involving the reaction of a target sample with a biomolecular array including one or more probe sets, where each probe set is a collection of one or more probes. The method includes receiving a set of values and using the set of values to generate for each probe set a first probability value indicating the probability that a molecular species complementary to the probe set is not present in the target sample. Each of the set of values corresponds to the interaction of the target sample with one of the probes.

Implementations of the invention can include one or more of the following advantageous features. The first probability value for a probe set is generated by comparing the values for the probes in the probe set with a value for a calibration set. The calibration set includes a null set. Comparing the values for the probes in the probe set with the value for the calibration set includes using a likelihood ratio algorithm. Comparing the values for the probes in the probe set with the value for the calibration set includes using an order statistics algorithm. The method includes using the set of values to generate for at least one probe set one or more second probability values indicating the probability that the molecular species complementary to the probe set is present at a level greater than or less than a reference concentration. The one or more second probability values for a probe set are generated by comparing the values for the probes in the probe set with values for the calibration set. The method includes using the first and second probability values to generate a normalized value for at least one probe set. Using the first and second probability values to generate a normalized value includes generating an interpolated value on a curve defined by the values for the calibration set. The calibration set includes a set of spiked probes. The calibration set includes a set of endogenous housekeeping genes. The collection of probes includes a collection of nucleic acid probes and using the set of values includes generating for at least one probe set a first probability value indicating the probability that a nucleic acid transcript complementary to the probe set is not present in the target sample. The method includes outputting an output file including the normalized value for at least one probe set. The normalized value for the at least one probe set includes a gamma-normalized value for the at least one probe set. The normalized value for the at least one probe set includes a principal component score for the at least one probe set. The normalized value for the at least probe set includes a cumulative distribution function score for the at least probe set. The method includes outputting an output file comprising the first and second probability values for at least one probe set.

In general, in another aspect, the invention features a method of analyzing a plurality of experiments involving the reaction of a target sample with a biomolecular array including one or more probe sets, where each probe set is a collection of one or more probes. The method includes receiving a plurality of data files, using the values to generate a normalized score for at least one probe set in two or more of the plurality of experiments, and comparing one or more normalized scores for two or more of the plurality of experiments. Each data file includes a set of values for an experiment. Each value corresponds to the interaction of the target sample with one of the probes for one of the plurality of experiments.

Implementations of the invention can include one or more of the following advantageous features. The normalized score includes a gamma-normalized value. The normalized score includes a principal component score. The normalized score includes a common factor score. The normalized score includes an empirical cumulative distribution score. At least one of the plurality of data files is received from a database.

In general, in another aspect, the invention features a method of generating a calibration set for use in analyzing a plurality of experiments involving the reaction of a target sample with a biomolecular array, where each array includes one or more probe sets and each probe set is a collection of one or more probes. The method includes receiving a plurality of data files, identifying from the data files one or more values corresponding to a set of null probes, a plurality of values corresponding to a predetermined set of spiked probes, and a plurality of values corresponding to a predetermined set of housekeeping probes expected to be present in the target sample for each of the plurality of experiments at a plurality of approximately known concentrations. Each data file includes a set of values for an experiment. Each value corresponds to the interaction of the target sample with one of the probes for one of the plurality of experiments.

Implementations of the invention can include one or more of the following advantageous features. The method includes using the values for the set of null probes, the set of spiked probes and the set of housekeeping probes to calculate a normalized score for each of the probe sets, and using the normalized scores to identify a new set of housekeeping probes.

In general, in another aspect, the invention features a computer program on a computer-readable medium for analyzing an experiment involving the reaction of a target sample with a biomolecular array, where the array includes one or more probe sets and each probe set is a collection of one or more probes. The program includes instructions operable to cause a programmable processor to receive a set of values and use the set of values to generate for at least one probe set a first probability value indicating the probability that a molecular species complementary to the probe set is not present in the target sample. Each value corresponds to the interaction of the target sample with one of the probes.

Implementations of the invention can include one or more of the following advantageous features. The instructions operable to generate the first probability value for a probe set include instructions operable to compare the values for the probes in the probe set with a value for a calibration set. The calibration set includes a null set. The instructions operable to compare the values for the probes in the probe set with the value for the calibration set include instructions to use a likelihood ratio algorithm. The instructions operable to compare the values for the probes in the probe set with the value for the calibration set include instructions to use an order statistics algorithm. The computer program includes instructions operable to cause a programmable processor to use the set of values to generate for at least one probe set one or more second probability values indicating the probability that the molecular species complementary to the probe set is present at a level greater than or less than a reference concentration. The instructions operable to use the set of values include instructions operable to compare the values for the probes in the probe set with values for the calibration set. The computer program includes instructions operable to cause a programmable processor to use the first and second probability values to generate a normalized value for at least one probe set. The instructions operable to use the first and second probability values to generate a normalized value include instructions operable to generate an interpolated value on a curve defined by the values for the calibration set. The calibration set includes a set of spiked probes. The calibration set includes a set of endogenous housekeeping genes. The collection of probes includes a collection of nucleic acid probes and the instructions operable to use the set of values include instructions operable to generate for at least one probe set a first probability value indicating the probability that a nucleic acid transcript complementary to the probe set is not present in the target sample. The computer program includes instructions operable to cause a programmable processor to output an output file including the normalized value for at least one probe set. The normalized value for the at least one probe set includes a gamma-normalized value for the at least one probe set. The normalized value for the at least one probe set includes a principal component score for the at least one probe set. The normalized value for the at least one probe set includes a cumulative distribution function score for the at least one probe set. The computer program includes instructions operable to cause a programmable processor to output an output file comprising the first and second probability values for at least one probe set.

In general, in another embodiment, the invention features a computer program on a computer-readable medium for analyzing a plurality of experiments involving the reaction of a target sample with a biomolecular array, where each array includes a one or more probe sets, and where each probe set is a collection of one or more probes. The computer program includes instructions operable to cause a programmable processor to receive a plurality of data files, use the values to generate a normalized score for at least one probe set in two or more of the plurality of experiments, and compare one or more normalized scores for two or more of the plurality of experiments. Each data file includes a set of values for an experiment. Each value corresponds to the interaction of the target sample with one of the probes for one of the plurality of experiments.

Implementations of the invention can include one or more of the following advantageous features. The normalized score includes a gamma-normalized value. The normalized score includes a principal component score. The normalized score includes a common factor score. The normalized score includes an empirical cumulative distribution score. At least one of the plurality of data files is received from a database.

In general, in another aspect, the invention features a data analysis system for analyzing an experiment involving the reaction of a target sample with a biomolecular array, where the array includes one or more probe sets, and where each probe set is a collection of one or more probes. The system includes means for receiving a set of values and means for using the set of values to generate for at least one probe set a first probability value indicating the probability that a molecular species complementary to the probe set is not present in the target sample. Each value corresponds to the interaction of the target sample with one of the probes.

Implementations of the invention can include one or more of the following advantageous features. The system includes means for using the set of values to generate for at least one probe set one or more second probability values indicating the probability that the molecular species complementary to the probe set is present at a level greater than or less than a reference concentration.

In general, in another embodiment, the invention features a database on a computer readable medium. The database includes a set of experimental values derived from an experiment and a normalized value for at least one probe set. The experiment includes the reaction of a target sample with a biomolecular array. The arrays include one or more probe sets. Each probe set is a collection of one or more probes. Each value in the set of experimental values corresponds to the interaction of the target sample with one of the probes. The normalized value is derived from the experimental values for the probes of the probe set.

Implementations of the invention may include one or more of the following advantageous features. The normalized values are gamma normalized values. The normalized values are principal component scores. The normalized values are cumulative distribution function scores. The database includes a set of probability values for at least one probe set for comparing the concentration of a molecular species in the target sample complementary to the probe set with a plurality of concentrations for probes in a calibration set.

Advantages that can be seen in implementations of the invention include one or more of the following. Derivation of probability values from measured properties enables the user to assess the quality of data and the likely error in the experiment. Foreign material, such as exogenous nucleic acid sequences, introduced at known concentrations provides a means for quantifying concentration of complementary species in a target sample. Endogenous nucleic acid sequences, expected or determined to be present at known and stable concentrations across samples, are used to quantify concentration levels for data derived from experiments involving one or more arrays. Statistical methods are used to normalize experimental data, compensating for systematic variation between experiments and allowing the comparison of data from multiple chips, including data resulting from experiments conducted at different times or under different conditions. Storage and use of normalized data enables the user to create and use databases of experimental information, making possible the comparison of large quantities of data from diverse sources. Sets of normalized database information from multiple samples can be used to design virtual or ad hoc experiments involving the comparison of samples selected for specific characteristics. Data used in such experiments can be dynamically normalized across the selected data sets to further improve the accuracy of data comparison and to indicate the quality of the data sets.

The details of one or more embodiments of the invention are set forth in the accompanying drawings and the description below. Other features and advantages of the invention will become apparent from the description, the drawings, and the claims.

BRIEF DESCRIPTION OF THE DRAWINGS

Like reference numbers and designations in the various drawings indicate like elements.

DETAILED DESCRIPTION

Methods and apparatus of the invention analyze and process biomolecular interaction data so as to enable the meaningful comparison of data from different experiments. In one embodiment, gene expression data extracted from a hybridization experiment can be used to answer two basic questions: first, whether a given gene is present or absent in an unknown sample; and second, if the gene is present, in what concentration. The data is normalized for comparison to data from other experiments. Data is stored to generate a database of information for use in other experiments.

Figure 1:
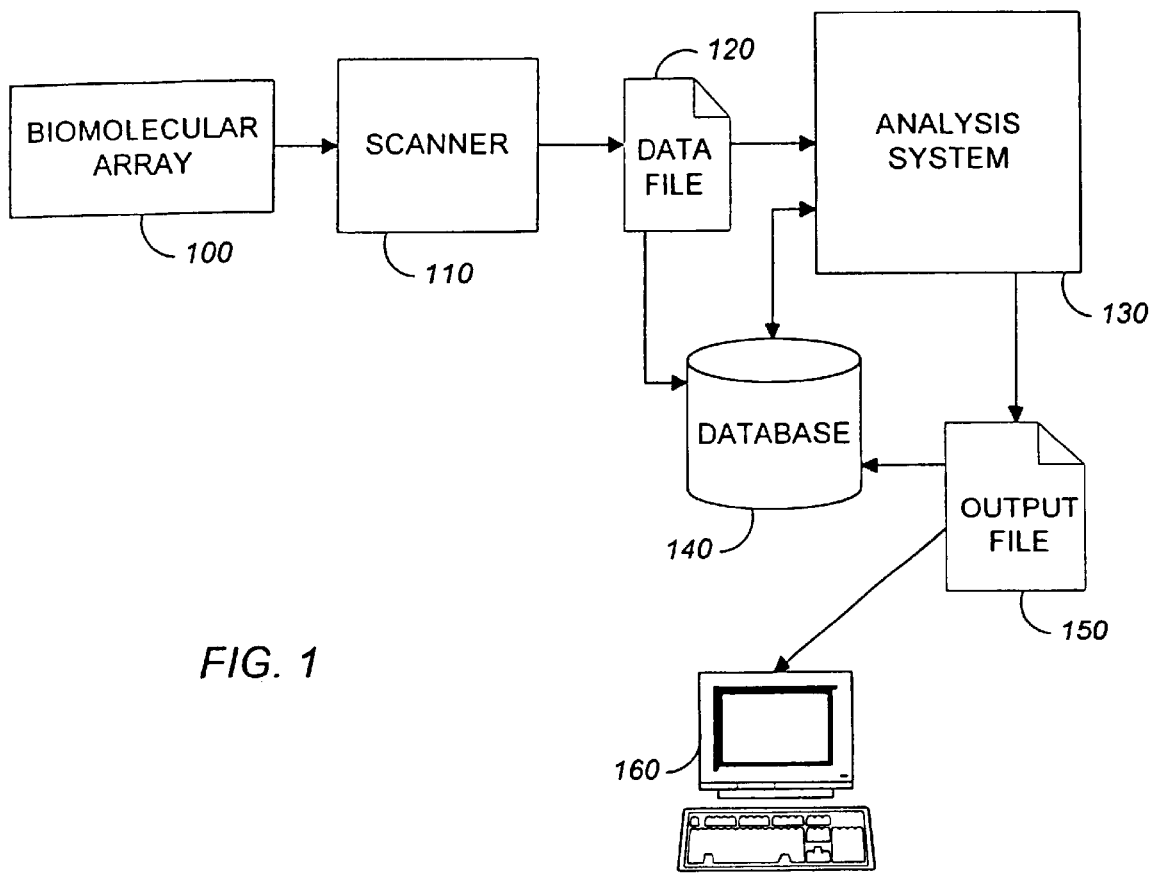
FIG. 1 is a block diagram illustrating a system implementing the invention.

FIG. 1 illustrates a computer system for analyzing experimental data from biomolecular arrays. An array 100 includes a large number of addressable molecular "probes" bound or deposited at known or determinable locations of the array. Arrays 100 include, for example, arrays of biomolecular probes bound to solid substrates or deposited in specific wells of a multi-well plate assay. Appropriate probe molecules include, for example, nucleic acids (including cDNAs and PCR amplification products), peptides, carbohydrates, and naturally-occurring or synthetic fragments thereof, as well as naturally occurring or synthetic small molecule ligands capable of specific binding to biomolecules. Probes may be molecules of known or unknown structure, and may correspond to reference molecules. Probes are addressable by x,y coordinates in two-dimensional arrays, x,y,z coordinates in three-dimensional arrays, well number in multi-well plate assays, isoelectric point and/or mass and relative position to a master gel for protein gel substrates, fiberoptic probe identification, or other known identification techniques. In specific embodiments, arrays 100 include, for example, nucleic acid arrays such as the line of GeneChip arrays available from Affymetrix, Inc., of Santa Clara, Calif., arrays of antibodies or antigens, carbohydrates or lectins.

In some embodiments it is advantageous to process and analyze experimental results from collections of probes at different addresses, referred to as "probe sets," which share one or more characteristics of interest in the analysis. Thus, for example, a nucleic acid array may include a number of individual oligonucleotide probes selected from various regions of an associated gene or gene fragment. The collection of probes corresponding to a particular gene may be considered a probe set for purposes of analyzing gene expression levels in a target sample. Such oligonucleotides may be "perfect match" oligonucleotides corresponding exactly to the sequence of the relevant portion of the gene or "mismatch" oligonucleotides identical in sequence to the perfect match except at one or more mismatched base positions.

The individual probes of array 100 function as addressable biomolecular detectors for detecting the presence of complementary molecular species in a known or unknown target sample. The target sample is introduced into or onto array 100, and the interaction between molecular species in the target sample with the detector probes of array 100 is observed in scanner 110, which measures a property associated with the specific binding or interaction of the molecular species in the target sample with the detector probes disposed on array 100. Measurable properties include concentration, affinity of interaction between the species and detector probe, molecular weight, extent of glycosylation, phosphorylation or other post-translational modification, and the like. Properties can be measured in scanner 100 based on changes in absorbance, fluorescence, refractive index (including surface plasmon resonance and optical guide index), or other spectroscopic changes, as well as changes in mass, acoustic wave detection, piezoelectric measurements, capacitive changes, conductivity or any other known measurable quantity. The use of probe sets that include multiple probes provides a degree of redundancy, making it possible to partition the total variation within an observed data set from multiple samples into variation due to specific probes ("probe error", such as, for example, where one fluorescence-labeled target oligonucleotide fluoresces more brightly than others upon hybridization with a complementary oligonucleotide probe), random error, and experimental factors, and to determine whether such factors significantly influence concentration levels between experiments.

Scanner 100 thus observes the molecular interaction and outputs a data file 120 including a value for the measured property (for example, the photon count for a fluorescence-based detection system) as a function of address or position on the substrate. Commercially available analysis tools, such as the GeneChip system, available from Affymetrix, Inc., of Santa Clara, Calif., measure the intensity at each location on the chip and record the data in the Genetic Analysis Technology Consortium standard "CEL file" format. Data file 120 is provided to analysis system 130, which can be based on any of a variety of computer systems. Analysis system 130 obtains data file 120 directly from scanner 110 or by retrieving data file 120 from memory, such as database 140. Analysis system 130 performs the analysis methods of the present invention, providing output files 150, which can be viewed on output devices 160 and/or stored in database 140.

Figure 2:
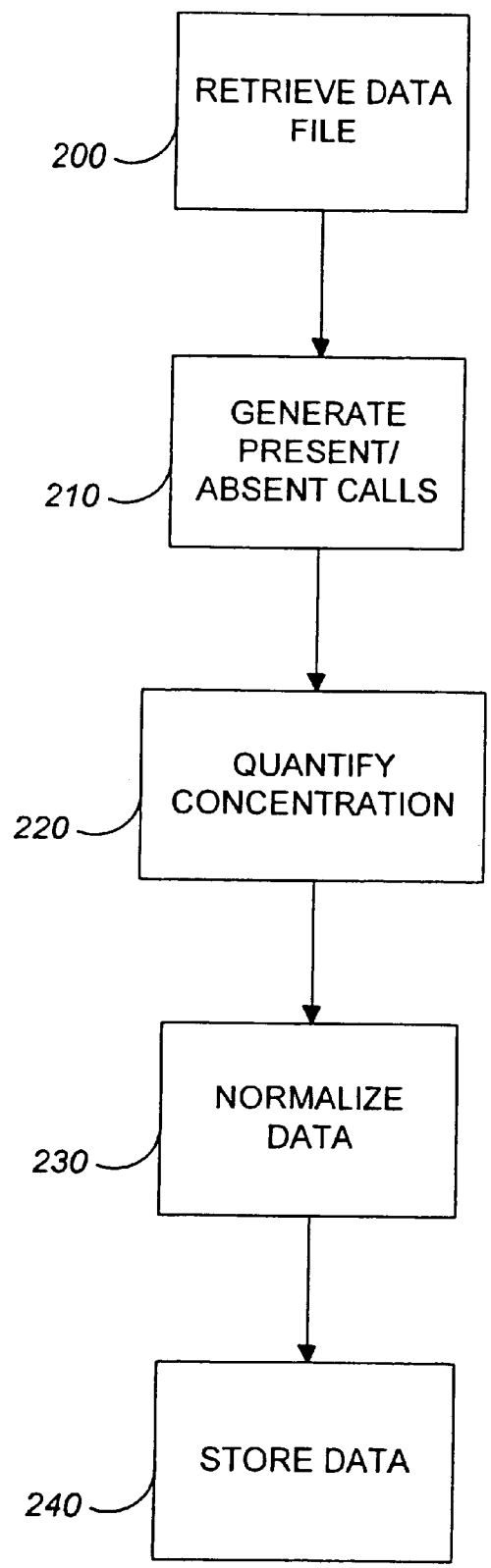
FIG. 2 is a flow diagram illustrating a process of analyzing experimental data according to the invention.

FIG. 2 illustrates the overall flow of data in one embodiment of analysis system 130. Analysis system 130 retrieves experimental data in the form of a data file, such as the CEL file mentioned above, containing intensity values observed in a DNA hybridization experiment (step 200). The system processes the data to derive a series of probability values ("P-values") corresponding to the probability that a gene represented by each probe set on the array is not present in the unknown sample, as will be described in more detail below (step 210). Analysis system 130 also derives a series of P-values corresponding to the probability that the gene corresponding to each probe set is present at each of one or more reference concentrations, as will be described in more detail below (step 220). Analysis system 130 calculates normalized values that can be compared with data collected in other experiments (step 230). Finally, analysis system 130 creates a database of normalized hybridization data for use in further analysis and experimentation (step 240).

Within Chip Analysis

Null Set Method

The probability that a gene is expressed in the target sample (i.e., the probability that an RNA transcript compatible with the probe set corresponding to the gene is present or absent in the target) is determined by comparing the observed values for the probes in that probe set with values observed for a set of probes that is known to be absent from the target sample. The set of absent probes will be referred to as the "null set" and may be incorporated into the array by design or identified empirically, such as, for example, probes falling in a lower predetermined quantile of the measured intensity data. In one embodiment, prior to analysis, the observed values are transformed according to one of the transformations set out in Table 1 below (where "PM" is the observed experimental value for a perfect match oligonucleotide and "MM" is the value for a mismatch oligonucleotide).

TABLE 1

Figure 3:
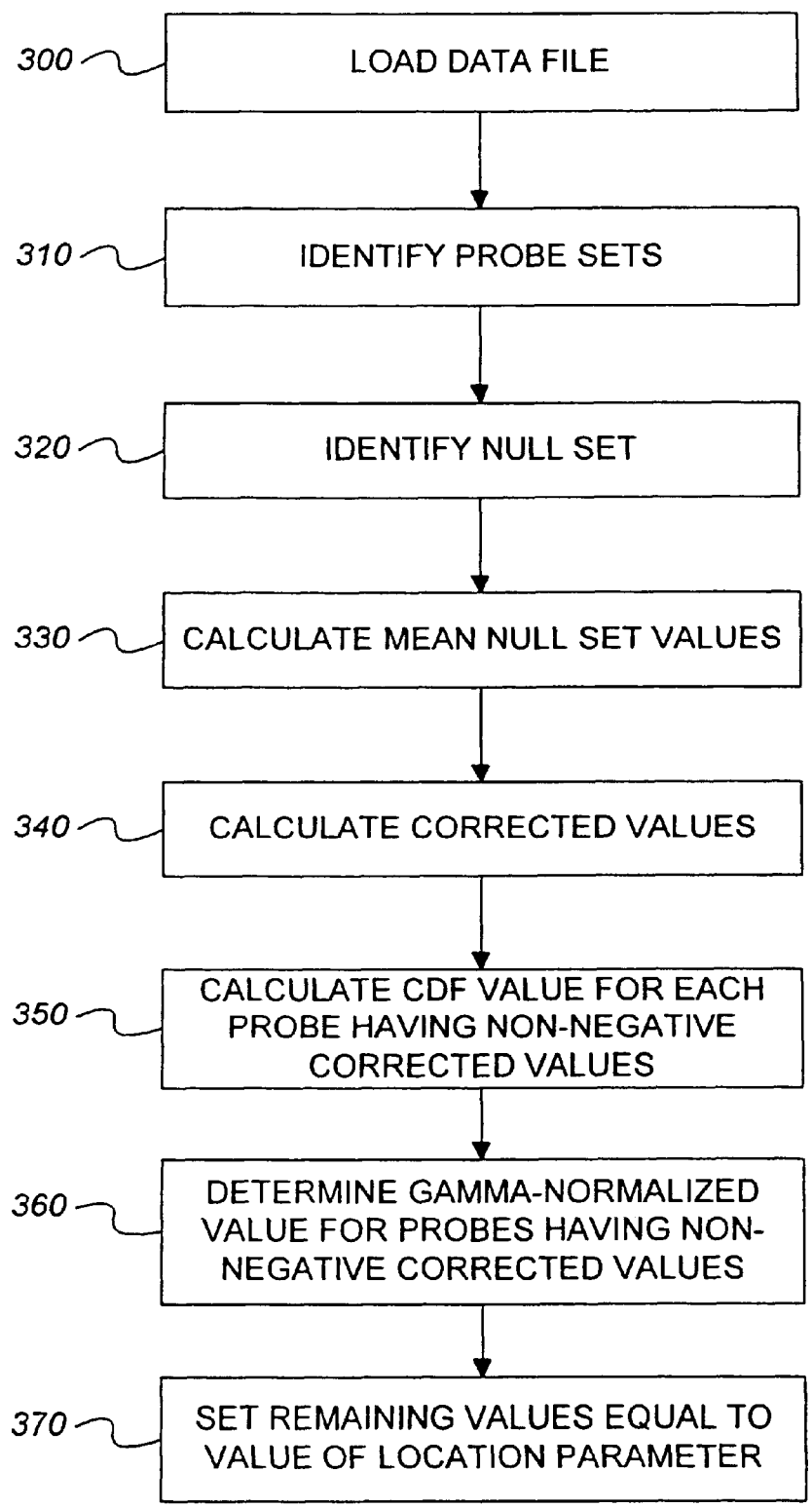
FIG. 3 is a flow diagram illustrating a process of gamma normalization of experimental data.

Data Transformations $D = PM - MM$
$SD = \sqrt{PM} - \sqrt{MM}$
$LD = \log_{10} PM - \log_{10} MM$
$PM$
$SPM = \sqrt{PM}$
$LPM = \log_{10} PM$ In another embodiment, the observed values are normalized prior to analysis by fitting the data to the gamma distribution as illustrated in FIG. 3. Analysis system 130 retrieves the experimental data (step 300) and identifies each of the probe sets on the chip from which the data is derived (obtained, for example, from data files supplied by the chip manufacturer) (step 310). Analysis system 130 identifies the null set based, for example, on the user's knowledge of null set probes incorporated into chip design or empirical observation of low intensity probe sets (step 320). The null set corresponds to transcripts known or expected to be not present in the target sample with any significant frequency. Such transcripts may be derived from exogenous sequences drawn from foreign genetic material, such as a bacterial or viral sequence, which are routinely provided on commercially available DNA arrays. The null set can also include nonsense sequences, reversed (but not complemented) variants of endogenous sequences and/or sequences endogenous to—but not expressed in—the source of the target sample. In either case, the probes that make up the null set are sequences that are known or expected to be not present in the target sample with any significant frequency.

Using the observed experimental values for null set probes, analysis system 130 calculates a mean value for the probes in the null set (step 330), and calculates a corrected value for each probe in the data set by subtracting the mean null set value from the observed value for each probe (step 340). Alternatively, corrected values are determined by subtracting values for mismatch probes or other measures of background.

For each probe having non-negative corrected value, analysis system 130 calculates an empirical cumulative density function value R (step 350). To do so, analysis system 130 counts the number (N) of non-negative corrected values in the data set and sorts the non-negative values in ascending order. For a given probe, the cumulative density function value equals the number of probes in the data set having corrected values less than or equal to the probe's corrected value divided by N−1.

For each R, analysis system 130 determines a corresponding gamma-normalized value by calculating an inverse gamma value from a gamma distribution having a fixed mean (which, for the gamma distribution, equals the sum of the location parameter and the product of the shape and scale parameters) (step 360). In one embodiment, the user fixes the mean a-priori by selecting specific appropriate values for the location, shape and scale parameters. Alternatively, analysis system 130 uses the non-negative corrected values to calculate the maximum likelihood estimates of the location, shape and scale parameters of the gamma distribution, using known methods, such as those disclosed in Norman L. Johnson & Samuel Kotz, *Distributions in Statistics: Continuous Univariate Distributions*—1 & 2 (Houghton Mifflin Co. 1970) and M. B. Wilk at al., "Estimation of parameters of the gamma distribution using order statistics," *Biometrika*, 49, 525–546 (1962). Analysis system 130 uses these estimates, or a combination of estimates for one or more parameters and user-selected values for the remaining parameters, to calculate the mean.

Analysis system completes the gamma normalization by setting any probe having a negative corrected value (as determined in step 340) equal to the value of the location parameter (step 370). Analysis system 130 uses this set of gamma-normalized values in place of the transformed values in the procedures discussed below.

Figure 4:
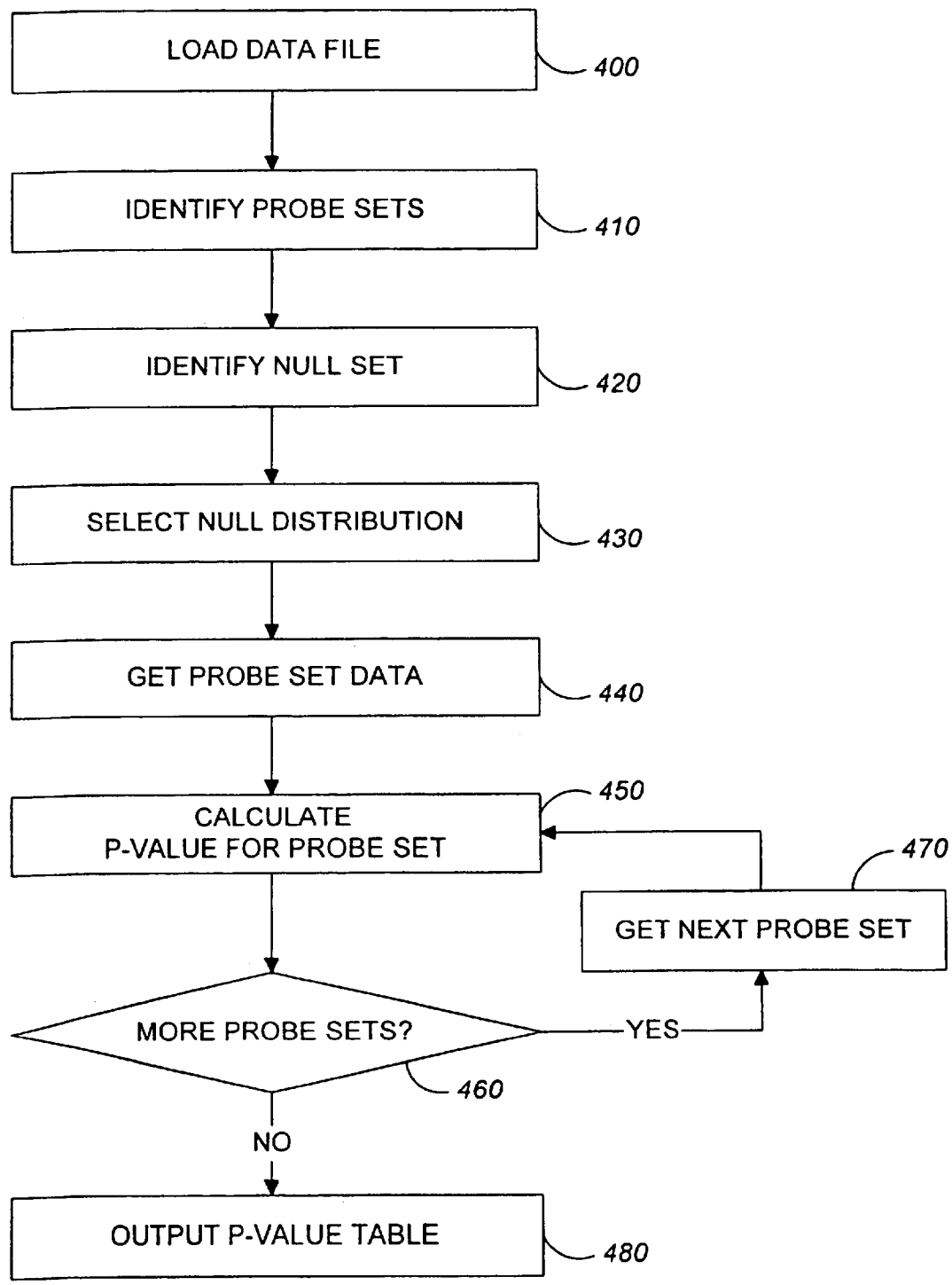
FIG. 4 is a flow diagram illustrating a process of determining a set of probability values indicating the likelihood that a molecular species is absent from a sample.

The process of determining a P-value for a given probe set is illustrated in FIG. 4. Analysis system 130 retrieves the experimental data, identifies the probe sets on the chip and identifies the null set as described above (steps 400–420). Analysis system 130 generates a null distribution of the transformed values for genes that are absent from the experiment by fitting the transformed data observed for the null set probes to a known distribution, such as a gamma or a Weibull distribution (step 430). Analysis system 130 trims any outlying data points, for example, by disregarding any probes in the null set or any probe set falling more than one and a half interquartile ranges below the first quartile or more than one and a half interquartile ranges above the third quartile. This part of the process can be performed using commercially available software from SAS Institute, Inc. of Cary, N.C. For each probe set on the chip, analysis system 130 retrieves the data (step 440), transforms it according to one of the transformations described above, and compares this data with the null distribution, applying a likelihood ratio- or order statistics-based test to calculate the probability (the "P-value") that the observed data belongs to the same distribution as the null set (step 450). While more probe sets remain to be analyzed (the YES branch of step 460), analysis system 130 retrieves the data (step 470) and calculates appropriate P-value (step 450). Analysis system 130 outputs the results of these calculations as a file containing a table of entries corresponding to each probe set on the chip (step 480). For each probe set, the table includes a P-value indicating the probability that the transformed data for the probe set came from the null distribution (e.g., the probability that each gene is absent from the target sample), as well as the number of probes considered in each calculation.

The user can view the results in a spreadsheet form using a program such as Microsoft Excel. Because the data is presented in the form of probability values, the user can determine for him- or herself the threshold level of error (in the form of a false positive rate) to apply to the experimental results. Probability values from one experiment can be compared with those from other experiments because they are not affected by systematic "chip-wide" error, such as degradation of the target sample.

Spike Method

Analysis system 130 uses a similar method to calculate the probability that a given gene is present in the target at a given reference concentration in a collection of one or more reference concentrations. As described above, commercially available DNA arrays are tiled with probe sets for genes from foreign sources as well as probe sets for genes native to the source of the target sample. Based on information about the source of the target, the user can identify genes tiled on the array that are not expressed in the target sample. By "spiking" the target sample with precisely known concentrations of one or more oligonucleotides corresponding to such genes, the user enables analysis system 130 to calculate P-values corresponding to the likelihood that other, expressed genes in the target sample are present at levels comparable to the spike concentrations.

Before beginning the experiment, the user adds one or more spikes to the target sample at known concentrations. By adding different spikes at a wide range of concentrations (for example, from well below the likely concentration of the target sample, if known, to well above that concentration), the user creates a "ladder" covering a range of concentrations from relatively low to moderate to relatively high concentration. A ladder can include spikes at from three or four to ten or more different, known concentrations.

Figure 5:
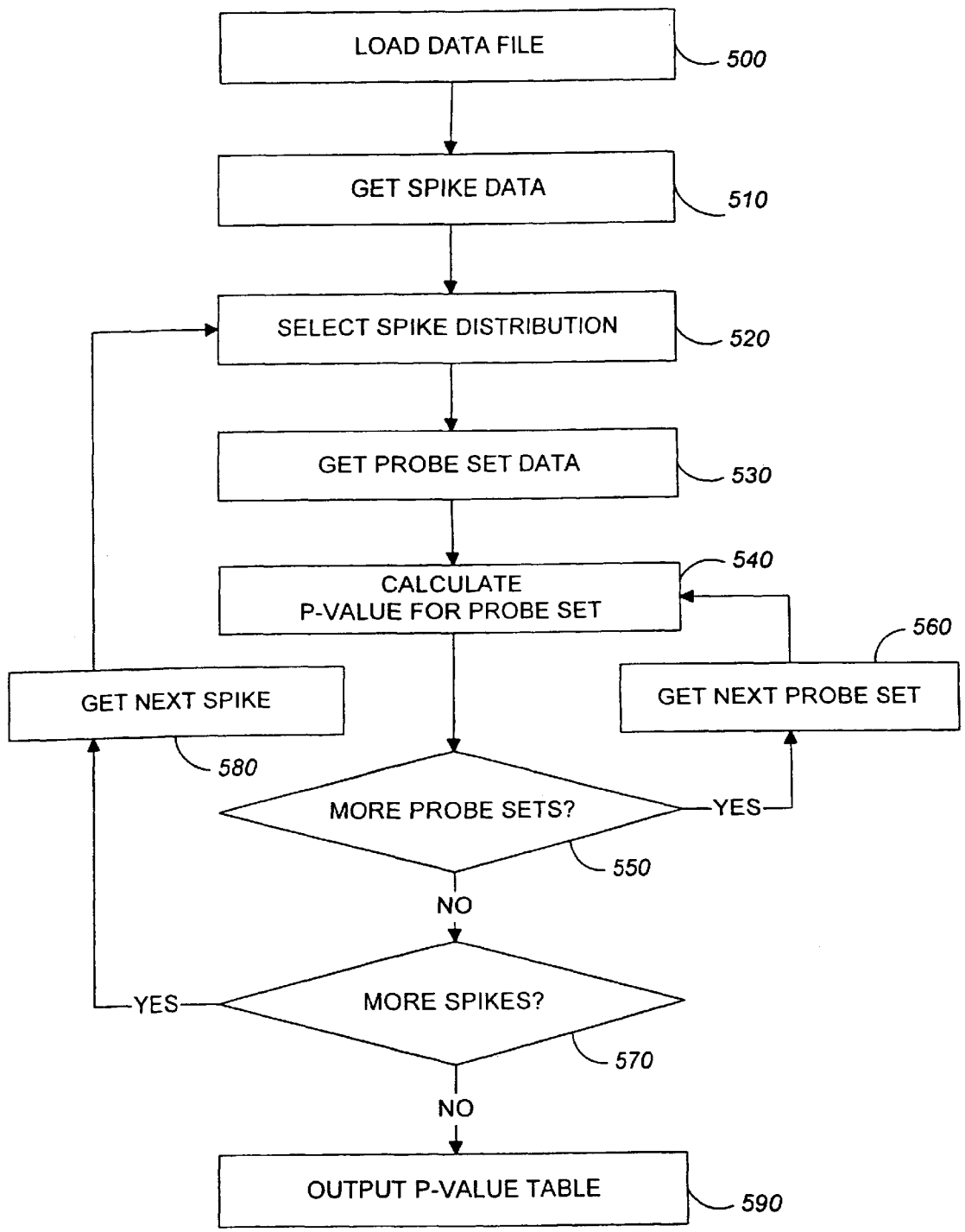
FIG. 5 is a flow diagram illustrating a process of determining a set of probability values indicating the likelihood that a molecular species is present in a sample at one or more known concentrations.

Analysis system 130 analyzes the data obtained from these spiked probe sets and applies the same likelihood ratio- or order statistics-based algorithms discussed above to calculate a P-value for each spike against the target, as illustrated in FIG. 5. Analysis system 130 loads the experimental data (step 500) and identifies spike probe sets based on information provided by the user (corresponding to the spikes added to the target sample at known concentrations) (step 510). After identifying, transforming and trimming (e.g., by using the interquartile method discussed above) experimental intensities for a spike probe set, analysis system 130 selects an appropriate distribution as described above in reference to the null distribution (step 520). Analysis system 130 retrieves, transforms and trims the experimental data for a probe set, as described above (step 530) and calculates a P-value for the spiked concentration against the target probe set—in other words, a value representing the probability that the target probe set falls in the same distribution as the spike (step 540). This P-value represents the likelihood that the target probe set is present in the target at a concentration close to that of the known spike concentration. While more probe sets remain to be tested against the spike (the YES branch of step 550), analysis system 130 retrieves and transforms the data for each of those probe sets (step 560) and calculates the corresponding P-value (step 540).

When all probe sets have been tested against a given spike (the NO branch of step 550), analysis system 130 turns to the remaining spikes (the YES branch of step 570), testing each of the probe sets to obtain a P-value for each spike against each probe set in turn (steps 580 and 520 through 540). When P-values have been obtained for all spikes against all probe sets in the target (the NO branch of step 570), analysis system 130 outputs a file including a table of P-values for each probe set in the array, as well as the number of probes used in the calculation for each probe set (step 590). In an alternative embodiment, analysis system 130 calculates a P-value for each spike against a given probe set before turning to the next probe set. This information and the P-values derived from the null set as discussed above essentially form a probability ladder, from which the user can identify the relative level at which the gene is present in the target sample on the scale of concentrations represented in the spike ladder.

Normalization of Chip Data

Analysis system 130 uses the null set and spike methods to normalize the experimental data for comparison to other experimental results.

Figure 6:
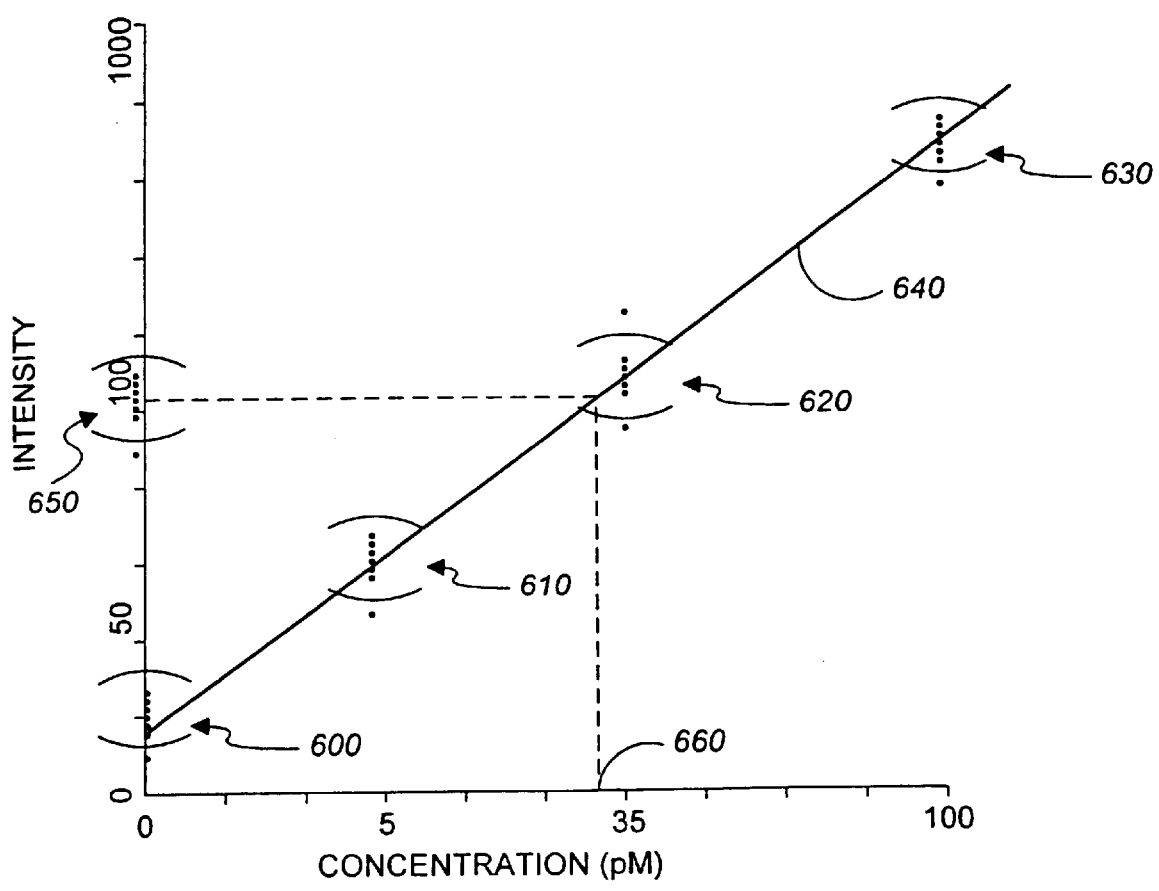
FIG. 6 is a graphical illustration of the process of normalizing data from an experiment.

FIG. 6 provides a graphical illustration of a probability ladder in the form of a plot of observed intensity versus known concentration for the null set 600 and spike probe sets 610, 620 and 630, which collectively form a "calibration set" for normalization of the experimental data. Analysis system 130 fits a curve 640 to the calibration set data using linear regression or other known techniques. Curve 640 can be used to derive a concentration value 660 for an unknown probe set having observed values 650. Thus, for example, using the spike ladder depicted in FIG. 6, analysis system 130 determines that the probe set having observed values 650 is present at a concentration that is greater than 5 picomolar, but less than 35 picomolar.

Analysis system 130 can calculate the variance of the known data points (i.e., the null set and spikes) from line 640, which can be used as a diagnostic of the quality of the chip and the experimental data. Analysis system 130 also calculates normalized values for the probe set values by projecting the data points onto curve 640. Analysis system 130 outputs a data file including a normalized value for each probe set on the chip.

Between Chip Analysis

Housekeeping Genes

Biological systems contain many thousands of genes. For example, there are approximately 100,000 genes in the human genome, only 10 to 30 percent of which are expressed at any one time. Of those, certain genes are consistently expressed in specific tissue types. For example, most tissues express similar levels of a gene known as GAPDH, which encodes a protein used in energy transport. Other genes are expressed at characteristic levels in specific tissue types. Such genes, which will be referred to as "housekeeping genes," can be added to the calibration set described above for use as an independent normalization criterion for data between chips or experiments.

A set of useful housekeeping genes can be predefined by the user. Alternatively, analysis system 130 identifies or extracts a set of appropriate housekeeping genes from a database of experimental data based on observed variability of expression levels across multiple experiments. Like the spike probes discussed above, it is advantageous for the set of housekeeping genes to span a broad dynamic range of expression, including genes consistently expressed at relatively low levels, moderate levels and relatively high levels.

Thus, it is advantageous to define or select a set of housekeeping genes that comprises a ladder of genes expressed at consistent, known levels. Table 2 identifies a list of housekeeping genes that have proven useful for the normalization methods of the invention (where NCBI Number is the identifying number assigned by the National Center for Biotechnology Information, DB identifies the database source—gb: GenBank; dbj: DataBank of Japan; emb: European Molecular Biology Laboratory, and Accession Number is the accession number in the corresponding database).

TABLE 2

Housekeeping Genes

| NCBI NUMBER | DB | ACCESSION NUMBER | DESCRIPTION |
| --- | --- | --- | --- |
| 1506275 | gb | AA034438 | AA034438 ze75f03.r1 Soares_fetal_heart_NbHH19W Homo sapiens cDNA clone IMAGE: 364829 5', mRNA sequence |
| 1525890 | gb | AA045978 | AA045978 z168e11.s1 Stratagene colon (#937204) Homo sapiens cDNA clone IMAGE: 509804 3' similar to SW: NUCM_BOVIN P17694 NADH-UBIQUINONE OXIDOREDUCTASE 49 KD SUBUNIT; contains element TAR1 repetitive element; mRNA sequence |
| 1696233 | gb | AA135106 | AA135106 zo24d04.s1 Stratagene colon (#937204) Homo sapiens cDNA clone IMAGE: 587815 3', mRNA sequence |
| 1860603 | gb | AA236173 | AA236173 zs05g05.s1 NCI_CGAP_GCB1 Homo sapiens cDNA clone IMAGE: 684344 3', mRNA sequence |
| 1891734 | gb | AA256131 | AA256131 zr79f02.s1 Soares_NhHMPu_S1 Homo sapiens cDNA clone IMAGE: 681915 3', mRNA sequence |
| 1940406 | gb | AA292427 | AA292427 zt28g07.s1 Soares ovary tumor NbHOT Homo sapiens cDNA clone IMAGE: 714492 3' similar to TR: E91187 E91187 NMDA RECEPTOR GLUTAMATE-BINDING SUBUNIT. ;, mRNA sequence |
| 2099973 | gb | AA421148 | AA421148 zt79f11.s1 Soares_testis_NHT Homo sapiens cDNA clone IMAGE: 728589 3', mRNA sequence |
| 2103099 | gb | AA424129 | AA424129 zv81a02.s1 Soares_total_fetus_Nb2HE8_9w Homo sapiens cDNA clone IMAGE: 760010 3', mRNA sequence |
| 2111862 | gb | AA428243 | AA428243 zw51d07.s1 Soares_total_fetus_Nb2HF8_9w Homo sapiens cDNA clone IMAGE: 773581 3' similar to TR: E236822 E236822 HYPOTHETICAL 26.5 KD PROTEIN. ;, mRNA sequence |
| 2184185 | gb | AA459278 | AA459278 zx89a02.s1 Soares ovary tumor NbHOT Homo sapiens cDNA clone IMAGE: 810890 3', mRNA sequence |
| 2205148 | gb | AA476937 | AA476937 zu38d11.s1 Soares ovary tumor NbHOT Homo sapiens cDNA clone IMAGE: 740277 3', mRNA sequence |
| 2261849 | gb | AA521306 | AA521306 aa79g06.s1 NCI_CGAP_GCB1 Homo sapiens cDNA clone IMAGE: 827194 3', mRNA sequence |
| 2432544 | gb | AA598872 | AA598872 ae37b10.s1 Gessler Wilms tumor Homo sapiens cDNA clone IMAGE: 897979 3', mRNA sequence |
| 2055255 | dbj | AB003177 | AB003177 Homo sapiens mRNA for proteasome subunit p27, complete CDs |
| 2647407 | dbj | AB009010 | AB009010 Homo sapiens mRNA for polyubiquitin UbC, complete CDs |
| 2460199 | gb | AF020833 | AF020833 Homo sapiens eukaryotic translation initiation factor 3 subunit (p42) mRNA, complete CDs |
| 2914752 | gb | AF035262 | AF035262 Homo sapiens BAF57 (BAF57) gene, complete CDs |
| 2828146 | gb | AF042384 | AF042384 Homo sapiens BC-2 protein mRNA, complete CDs |
| 3095112 | gb | AF053070 | AF053070 Homo sapiens NADH: ubiquinone dehydrogenase 51 kDa subunit (NDUFV1) mRNA, nuclear gene encoding mitochondrial protein, complete CDs |
| 3152659 | gb | AF064603 | AF064603 Homo sapiens GA17 protein mRNA, complete CDs |
| 3599572 | gb | AF089750 | AF089750 Homo sapiens flotillin-1 mRNA, complete CDs |
| 3659900 | gb | AF092124 | AF092124 Homo sapiens F1F0-type ATP synthase subunit g mRNA, complete CDs |

TABLE 2-continued

Housekeeping Genes

| NCBI NUMBER | DB | ACCESSION NUMBER | DESCRIPTION |
|---|---|---|---|
| 3483018 | emb | AJ010569 | HSA010569 Homo sapiens mRNA for GEF-2 protein |
| 219612 | dbj | D12686 | HUMEIF4G Human mRNA for eukaryotic initiation factor 4 gamma (eIF-4 gamma) |
| 285948 | dbj | D14662 | HUMORF06 Human mRNA for KIAA0106 gene, complete CDs |
| 1037163 | dbj | D38047 | HUMPSP31 Human mRNA for 26S proteasome subunit p31, complete CDs |
| 1808577 | dbj | D44466 | D44466 Homo sapiens mRNA for proteasome subunit p112, complete CDs |
| 665587 | dbj | D45887 | HUMALDN Human mRNA for calmodulin, complete CDs |
| 960918 | dbj | D59812 | D59812 HUM068G09A Clontech human fetal brain polyA+ mRNA (#6535) Homo sapiens cDNA clone GEN-068G09 3', mRNA sequence |
| 961447 | dbj | D63878 | D63878 Human mRNA for KIAA0158 gene, complete CDs |
| 1228038 | dbj | D83778 | D83778 Human mRNA for KIAA0194 gene, partial CDs |
| 670605 | emb | E03974 | E03974 HSC2FE122 normalized infant brain cDNA Homo sapiens cDNA clone c-2fe12 3', mRNA sequence |
| 1057868 | gb | H79779 | H79779 yu77h11.s1 Soares fetal liver spleen 1NFLS Homo sapiens cDNA clone IMAGE: 239877 3', mRNA sequence |
| 1059391 | gb | H81302 | H81302 yu74f06.s1 Soares fetal liver spleen 1NFLS Homo sapiens cDNA clone IMAGE: 239555 3', mRNA sequence |
| 1068774 | gb | H87195 | H87195 yw15h07.s1 Soares_placenta_8to9weeks_2NbHP8to9W Homo sapiens cDNA clone IMAGE: 252349 3', mRNA sequence |
| 340020 | gb | K00558 | HUMTUBAK human alpha-tubulin mRNA, complete CDs |
| 339204 | gb | L02648 | HUMTCN2B Homo sapiens (clone V6) transcobalamin II (TCN2) mRNA, complete CDs |
| 190949 | gb | L07872 | HUMRBPJKA Human Jk-recombination signal binding protein (RBPJK) gene exons 1–11, 5' end |
| 181536 | gb | L12136 | HUMDEOXDEA Homo sapiens (clone pCD12) deoxycytidylate deaminase mRNA, complete CDs |
| 414586 | gb | L25899 | HUMRP10A Human ribosomal protein L10 mRNA, complete CDs |
| 3334898 | gb | L38696 | HUMAUAG Homo sapiens autoantigen p542 mRNA, complete CDs |
| 177967 | gb | M10277 | HUMACCYBB Human cytoplasmic beta-actin gene, complete CDs |
| 184371 | gb | M18930 | HUMHPSNA Human hepsin mRNA, complete CDs |
| 178042 | gb | M19283 | HUMACTGA Human cytoskeletal gamma-actin gene, complete CDs |
| 184102 | gb | M23115 | HUMHK2A Homo sapiens calcium-ATPase (HK2) mRNA, complete CDs |
| 189271 | gb | M23613 | HUMNPM Human nucleophosmin mRNA, complete CDs |
| 337504 | gb | M31520 | HUMRPS24A Human ribosomal protein S24 mRNA |
| 182976 | gb | M33197 | HUMGAPDH Human glyceraldehyde-3-phosphate dehydrogenase (GAPDH) mRNA, complete CDs |
| 190827 | gb | M63167 | HUMRACPC Human rac protein kinase alpha mRNA, complete CDs |
| 183265 | gb | M84443 | HUMGLTKIN H. sapiens galactokinase (GK2) mRNA, complete CDs |
| 189952 | gb | M86400 | HUMPHPLA2 Human phospholipase A2 mRNA, complete CDs |
| 1192398 | gb | N51232 | N51232 yz13c04.s1 Soares_multiple_sclerosis_2NbHMSP Homo sapiens cDNA clone IMAGE: 282918 3', mRNA sequence |
| 1196229 | gb | N54909 | N54909 yv34e04.s1 Soares fetal liver spleen 1NFLS Homo sapiens cDNA clone IMAGE: 244638 3', mRNA sequence |
| 834194 | gb | R62315 | R62315 yi17d10.s1 Soares placenta Nb2HP Homo sapiens cDNA clone IMAGE: 139507 3', mRNA sequence |

TABLE 2-continued

Housekeeping Genes

| NCBI NUMBER | DB | ACCESSION NUMBER | DESCRIPTION |
| --- | --- | --- | --- |
| 519935 | gb | T23695 | T23695 seq369 b4HB3MA-Cot18-Bio Homo sapiens cDNA clone b4HB3MA-Cot18-Bio-4 3', mRNA sequence |
| 614170 | gb | T32072 | T32072 EST43352 Human Brain Homo sapiens cDNA 3' end similar to None, mRNA sequence |
| 698109 | gb | T79600 | T79600 yd71c12.s1 Soares fetal liver spleen 1NFLS Homo sapiens cDNA clone IMAGE: 113686 3' similar to gb: J03544 GLYCOGEN PHOSPHORYLASE, BRAIN FORM (HUMAN);, mRNA sequence |
| 550022 | gb | U14971 | HSU14971 Human ribosomal protein 59 mRNA, complete CDs |
| 1045573 | gb | U37012 | HSU37012 Human cleavage and polyadenylation specificity factor mRNA, complete CDs |
| 1017822 | gb | U37689 | HSU37689 Human RNA polymerase II subunit (hsRPB8) mRNA, complete CDs |
| 1718196 | gb | U46025 | HSU46025 Human translation initiation factor eIF-3 p110 subunit gene, complete CDs |
| 3849817 | gb | U58675 | U58675 Homo sapiens Chromosome 17p13 Cosmid Clone cos39, complete sequence |
| 1913895 | gb | U90915 | HSU90915 Human clone 23600 cytochrome c oxidase subunit IV mRNA, complete CDs |
| 32449 | emb | V00530 | HSHPRT Human mRNA encoding IMP: pyrophosphate phosphoribosyltransferase E.C. 2.4.2.8 |
| 1378408 | gb | W69127 | W69127 zd44f02.s1 Soares_fetal_heart_NbHH19W Homo sapiens cDNA clone IMAGE: 343515 3' similar to PIR: C48827 C48827 zinc finger protein = meiosis-associated DNA-binding regulatory [1] ;, mRNA sequence |
| 1382621 | gb | W72154 | W72154 zd70g07.s1 Soares_fetal_heart_NbHH19W Homo sapiens cDNA clone IMAGE: 346044 3' similar to SW: LEG4_RAT P38552 GALECTIN-4 ;, mRNA sequence |
| 1400545 | gb | W86756 | W86756 zh64f03.s1 Soares_fetal_liver_spleen_1NFLS_S1 Homo sapiens cDNA clone IMAGE: 416861 3', mRNA sequence |
| 1401768 | gb | W87714 | W87714 zh65d12.s1 Soares_fetal_liver_spleen_1NFLS_S1 Homo sapiens cDNA clone IMAGE: 416951 3' similar to gb: X7575S_rna2 SPLICING FACTOR SC35 (HUMAN);, mRNA sequence |
| 29550 | emb | X05610 | HSC4A2 Human mRNA for type IV collagen alpha (2) chain |
| 30265 | emb | X12492 | HSCTF1 Human mRNA for CAAT-box binding transcription factor CTF-1 (syn. CTF/NFI or CTF or NF-I or NF-1) |
| 29890 | emb | X52192 | HSCFES H. sapiens RNA for c-fes |
| 30365 | emb | X54667 | HSCYSTATS H. sapiens mRNA for cystatin S |
| 23690 | emb | X56932 | HS23KDHBP H. sapiens mRNA for 23 kD highly basic protein |
| 441311 | emb | X72964 | HSCALT H. sapiens mRNA for caltractin |
| 2853173 | emb | Y13286 | HSY13286 Homo sapiens mRNA for GDP dissociation inhibitor beta |
| 297142 | emb | Z22651 | HSHLA35A H. sapiens HLA-B35 mRNA |
| 587183 | emb | X39594 | Z39594 HSC1EC092 normalized infant brain cDNA Homo sapiens cDNA clone c-lec09 3', mRNA sequence |

Principal Component Analysis

Figure 7:
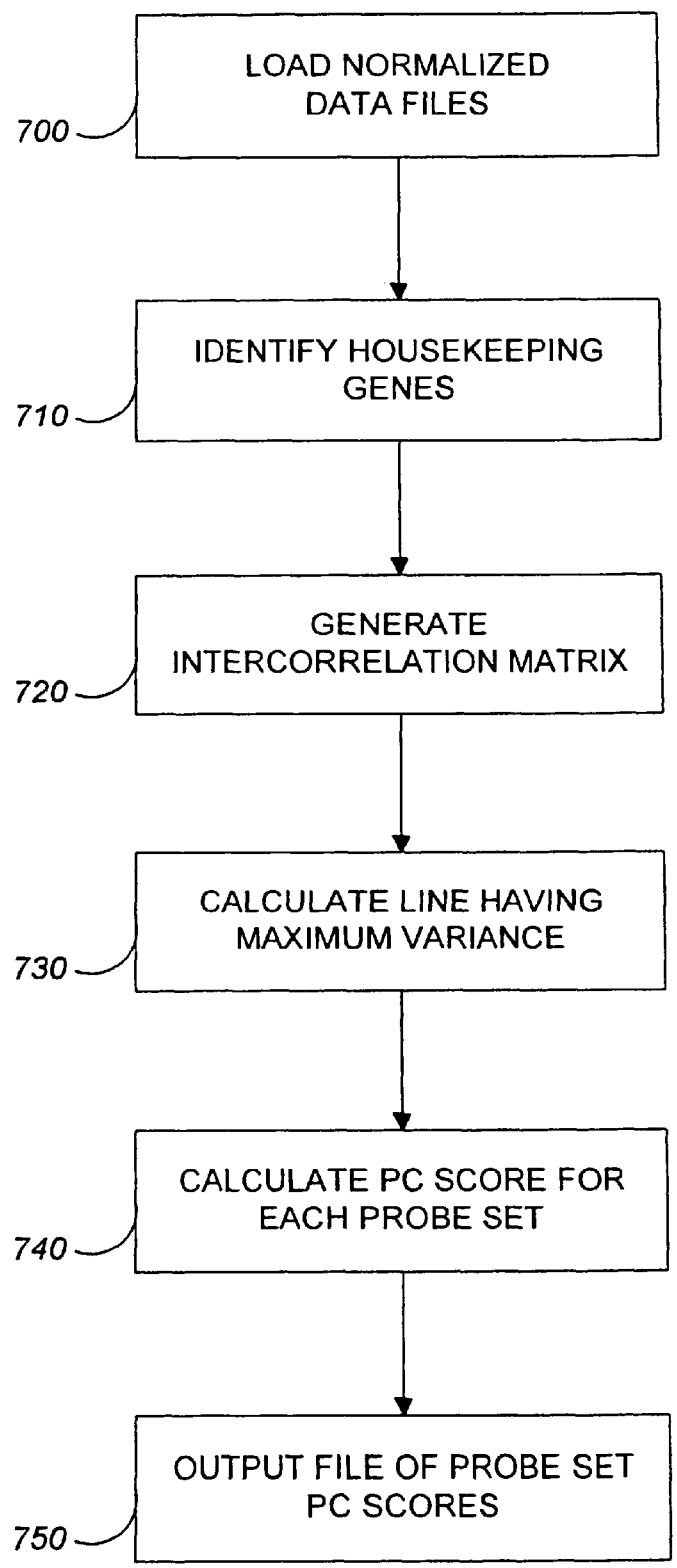
FIG. 7 is a flow diagram illustrating a process of normalizing data from multiple experiments.

Analysis system 130 uses data from the set of housekeeping genes to normalize the data between chips using the known statistical method of principal component analysis. The principal component analysis described below can be implemented using commercially available software packages, such as are available from SAS Institute of Cary, N.C. Referring to FIG. 7, to analyze data from a set of N experiments (for example, a database containing N samples of a given tissue type), analysis system 130 loads the normalized data file for each experiment (step 700) and identifies the housekeeping genes as described above (step 710). Analysis system 130 applies the known Blom transformation to the intensity values to force the data to approximate a multivariate normal distribution and generates an intercorrelation matrix reflecting the correlation between each pair of experiments (step 720). Analysis system 130 uses this data to calculate a line in the N dimensional data space, such that the set of values defined by the projection of the data set onto the line has maximum variance for the data set (i.e., the line along which the projections of the members of the data set are most distinct) (step 730). Analysis system 130 does this by decomposing the intercorrelation matrix in a conventional way to form a diagonal matrix of eigenvalues and a corresponding orthogonal matrix of eigenvectors. The largest eigenvalue divided by N is the proportion of the total variance between the N experimental samples that is accounted for by the line whose equation coefficients are given by the elements of the corresponding eigenvector. This value serves as a quantification of the adequacy of the normalization; outlier genes can be eliminated from the set of housekeeping genes, resulting in an improved normalization (i.e., one in which a higher proportion of total variance is accounted for by the first eigenvector).

Analysis system 130 then generates a principal component score (a "PC score") for each probe set of each experimental sample by projecting the stored intensity values onto the line defined by the first eigenvector (step 740). Analysis system 130 outputs a table of PC scores for each probe set of each sample (step 750). These scores can be used as normalized values for comparison across the N experimental samples. Analysis system 130 also reports the residual variance (the variance not accounted for by the largest eigenvalue), which can be used as a diagnostic of the quality of the normalization. Analysis system 130 can also quantify the normalization error by "re-normalizing" the data using the spike data in each experiment in the data set.

Optionally, analysis system 130 improves the results obtained from principal component analysis by using the known method of common factor analysis, which may also be implemented using commercially available statistics software packages. Analysis system 130 modifies the diagonal elements of the intercorrelation matrix generated in step 720 to reflect the commonality between each pair of samples according to known common factor analysis techniques. Analysis system 130 decomposes this matrix as described for step 730 above. Projection of intensity values for each probe set of each sample onto the resulting eigenvector yields "common factor scores" analogous to the PC scores described above. The common factor score can be used to compare values across experiments; incorporation of commonality into the calculation results in a more realistic modeling of the dependencies among the samples, with samples that are more representative of the group of samples being emphasized or weighted more in the comparison than outlying samples.

In another embodiment, instead of normalizing experimental values using principal component and/or common factor analysis, analysis system 130 uses the calibration set to generate an empirical cumulative distribution function ("cdf") as described above in reference to FIG. 3. Analysis system 130 uses this function to calculate a probability for each experimental or transformed value that a sample randomly chosen from the reference distribution would have a value at most equal to the value in question.

Databasing

The above-described within-chip analysis techniques are useful for comparing experimental values derived from a single experiment. For each experiment, analysis system 130 outputs a file that includes a series of P-values for each probe set for comparing the probe set with the null set, with each spike, and with specific members of the calibration set (e.g., indicating the probability that the gene is not expressed in the target sample and the probability that expressed genes are present at concentrations similar to those of individual members of the calibration set). The output file also includes a set of average normalized values (from gamma normalization, principal component/common factor normalization or cdf normalization, as discussed above) for each probe set on the chip. Optionally, the output file contains for each probe set P-values from statistical tests of the change between individual samples or groups of samples while controlling for systematic variability between probes in one or more experiments.

The above described between-chip techniques can be used for comparison of data across experiments. The generation of well-characterized databases enables analysis system 130 to offer users the ability to design virtual experiments by selecting specific samples from a database of experiments, for example comparing a series of samples drawn from healthy subjects with a series of samples drawn from patients having a specific type of tumor or disease. Storage of data in such databases enables the user to reassess the quality of data with each new experiment by renormalizing data across experiments with an ever-increasing number of relevant experimental samples. When the user selects a subset of samples from the database, analysis system 130 computes principal component scores for all genes in each sample as described above. Analysis system 130 removes statistical outliers from the sample set to generate a set of housekeeping genes optimized for the specific subset of samples, and uses these sample-specific housekeeping genes to recalculate principal component scores for the genes in question.

In one embodiment, such a database includes a data record for each experiment including such identifying information as the identity and condition of the patient or source organism, the tissue type and any relevant experimental conditions. Each record also includes a pointer indicating where the raw or normalized data is stored; alternatively, the data files are incorporated into the data record for the relevant experiment.

Analysis system 130 searches the database by obtaining a query from the user and generates a list of data records matching the search terms specified in the query. The user selects any desired data records and analysis system 130 normalizes the data for the selected records and performs the specified comparisons.

The usefulness of the within-chip and between-chip techniques described above is shown in the following example.

EXAMPLE

Time Course Study of Gene Expression of Monocyte-derived Macrophages (MDM)

Macrophages are implicated in tissue destruction observed in inflammatory disease. In this in-vitro study, monocytes were allowed to develop into macrophages over a period of 12 days. The purpose of this analysis was to identify genes whose expression level changes significantly over time, and cluster the identified genes by their expression level patterns over time.

Gene expression levels for samples taken at baseline (0 hours), 4 hours, 1 day, 6 days and 12 days were measured by hybridization of their RNA message population to the Affymetrix Human 6.8 k GeneChip. The methods used for the preparation of cRNA and the subsequent hybridization and scanning are described in commonly-assigned pending U.S. application Ser. Nos. 09/268,865 and 09/268,866, both filed on Mar. 15, 1999, which are incorporated herein by reference.

The data consisted of five intensity matrices, one recorded for each of the five time points. The chip design used in this analysis employs a subset of the perfect-match probes for each gene on the chip. The Affymetrix Human 6.8 k chip allows for interrogation of 7023 genes. The chip also includes 22 foreign genes, four of which were spiked at the following concentration levels:
1. *E. coli* BioB (1.5 pM)
2. *E. coli* BioC (5 pM)
3. *E. coli* BioD (25 pM)
4. Phage P1 Cre (100 pM). ps Probes from the 18 remaining foreign genes (Bacterial and Yeast) were used as the "Null Set" (i.e., concentration of zero).

The observed intensity levels were normalized using the procedures described above. The "calibration set" consisted of the "Null Set", the four spikes, and the following genes (GenBank Accession number in parentheses)
1. beta-actin (X00351)
2. glyceraldehyde-3-phosphate dehydrogenase (M33197)
3. *Homo sapiens* transcription factor ISGF-3 mRNA (M97935)
4. Human 18S rRNA gene (M10098)
5. Human transferrin receptor mRNA (M11507).

Application of the within-chip analysis described above to each of the five data matrices produced five P-values for each of the 7023 genes, corresponding to tests of hypotheses that the given gene is at a concentration similar to the "Null Set", BioB, BioC, BioD and Cre, respectively. The normalized average intensity was also calculated for each gene. An exemplary output table for the baseline (0 hours) sample is presented in Table 3.

the one-tailed test that a gene concentration is greater than the indicated reference.

AVGI: The gene normalized average intensity calculated from gamma normalized probe intensity values as described above.

This analysis allows the user to make statements about whether a given gene is present in the sample (PNULL) and to place the level of expression of the gene along the ladder of spikes by resolving the values of PBIOB, PBIOC, PBIOD, and PCRE. Considering, for example, row 12 of Table 3, the entry for gene AFFX-HUMRGE/M10098_5:

| PNULL | PBIOB | PBIOC | PBIOD | PCRE | AVGI |
|---|---|---|---|---|---|
| 0.000000 | 0.000054 | 0.001182 | (0.000254) | (0.000002) | 12742 |

For this gene, the analysis yields an average intensity of 12742 (AVGI), significantly higher than the "Null Set" (PNULL=0.00000), and also significantly higher than BioB and BioC; but the concentration of the gene is significantly lower than BioD and Cre, suggesting a concentration between the known concentrations of BioC and BioD.

Next, the between-chip methods described above were applied to ascertain which genes experience significant changes in concentration over time. A two-factor analysis of variance was carried out for each gene, the factors being time and probe, with repeated measures on the time factor with values of 0, 4, 24, 144, and 288 hours to test the null

TABLE 3

Exemplary Within-Chip Analysis Output

| PROBESET | PNULL | PBIOB | PBIOC | PBIOD | PCRE | AVGI |
|---|---|---|---|---|---|---|
| AFFX-HSAC07/X00351_3 | 0.000000 | 0.000000 | 0.000000 | 0.000040 | 0.015127 | 56206 |
| AFFX-HSAC07/X00351_5 | 0.000000 | 0.000000 | 0.000000 | 0.000012 | 0.029627 | 44850 |
| AFFX-HSAC07/X00351_M | 0.000000 | 0.000000 | 0.000000 | 0.000001 | 0.007465 | 48716 |
| AFFX-HUNGAPDH/M33197_3 | 0.000000 | 0.000000 | 0.000000 | 0.003673 | 0.338336 | 36843 |
| AFFX-HUMGAPDH/M33197_5 | 0.000000 | 0.000000 | 0.000000 | 0.000871 | 0.234818 | 37162 |
| AFEX-HUMGAPDH/M33197_M | 0.000000 | 0.000000 | 0.000000 | 0.000327 | 0.122864 | 41375 |
| AFFX-HUMISGF3A/M97935_3 | 0.047821 | 0.302711 | 0.471019 | (0.000526) | (0.000024) | 7277 |
| AFFX-HUMISGF3A/M97935_5 | (0.095012) | (0.000277) | (0.000038) | (0.000000) | (0.000000) | 135 |
| AFFX- | (0.317991) | (0.000782) | (0.000097) | (0.000000) | (0.000000) | 364 |
| AFFX- | (0.001190) | (0.000043) | (0.000007) | (0.000000) | (0.000000) | 64 |
| AFFX-HUMRGE/M10098_3 | 0.000001 | 0.084604 | 0.339911 | (0.000000) | (0.000000) | 6447 |
| AFFX-HUMRGE/M10098_5 | 0.000000 | 0.000054 | 0.001182 | (0.000254) | (0.000002) | 12742 |
| AFFX-HUMRGE/M10098_M | 0.000033 | 0.005247 | 0.015674 | (0.054037) | (0.003379) | 16234 |
| AFFX-HUMTFRR/M11507_3 | 0.103303 | (0.016859) | (0.002073) | (0.000000) | (0.000000) | 1311 |
| AFFX-HUMTFRR/M11507_5 | (0.000000) | (0.000017) | (0.000003) | (0.000000) | (0.000000) | 2 |
| AFFX-HUMTFRR/M11507_M | (0.000034) | (0.000031) | (0.000005) | (0.000000) | (0.000000) | 0 |
| AJ000099 | 0.000000 | 0.084080 | 0.395560 | (0.000000) | (0.000000) | 6040 |
| AJ000480 | 0.000000 | 0.000183 | 0.001748 | (0.003786) | (0.000045) | 14412 |
| AJ001047 | (0.226638) | (0.000575) | (0.000074) | (0.000000) | (0.000000) | 298 |
| AJ001421 | 0.000001 | (0.403516) | (0.093599) | (0.000000) | (0.000000) | 3423 |
| AJ001487 | 0.110704 | (0.008111) | (0.000915) | (0.000000) | (0.000000) | 929 |
| D00003 | (0.000000) | (0.000002) | (0.000001) | (0.000000) | (0.000000) | 0 |
| D00017 | 0.000000 | 0.000000 | 0.000006 | (0.071903) | (0.000970) | 19559 |
| D00097 | 0.139088 | (0.022426) | (0.003025) | (0.000000) | (0.000000) | 1406 |
| D00408 | 0.000000 | (0.064213) | (0.007043) | (0.000000) | (0.000000) | 1874 |
| D00591 | (0.323054) | (0.000474) | (0.000059) | (0.000000) | (0.000000) | 78 |
| D00596 | 0.215648 | (0.011771) | (0.001496) | (0.000000) | (0.000000) | 1132 |
| D00632 | 0.000524 | 0.384289 | (0.270105) | (0.000000) | (0.000000) | 4392 |
| D00654 | 0.141195 | (0.402360) | (0.226815) | (0.000014) | (0.000000) | 3991 |

The column headings in Table 3 are as follows:
PROBESET: Gene Accession Number or descriptor.
PNULL, PBIOB, PBIOC, PBIOD, PCRE: P-values as described above. P-values in parentheses are for the one-tailed test that a gene concentration is less than the indicated reference; P-values without parentheses are for hypothesis that there is no change over time. The use of probe number as the second factor in the experimental design results in the elimination of systematic inter-probe variability because each gene is measured by the same set of probes for every time point. The analysis of variance produces a P-value representing the statistical significance of the observed change over time (the probability that the observed change is due to chance alone) for each gene. An exemplary output is presented in Table 4.

TABLE 4

Exemplary Analysis of Variance (Between-Chip) Output

| CHIP | STRAND | PROBESET | p-TIME |
|---|---|---|---|
| 1 | A | A28102 | 0.235923 |
| 1 | A | AB000114 | 0.424078 |
| 1 | A | AB000115 | 0.490287 |
| 1 | A | AB000220 | 0.004171 |
| 1 | A | AB000381 | 0.424078 |
| 1 | A | AB000409 | 0.319014 |
| 1 | A | AB000410 | 0.007651 |
| 1 | A | AB000449 | 0.424078 |
| 1 | A | AB000450 | 0.006153 |
| 1 | A | AB000460 | 0.000000 |
| 1 | A | AB000462 | 0.065299 |
| 1 | A | AB000464 | 0.387512 |
| 1 | A | AB000466 | 0.481997 |
| 1 | A | AB000467 | 0.225938 |
| 1 | A | AB000468 | 0.062320 |
| 1 | A | AB000584 | 0.004291 |
| 1 | A | AB000816 | 0.424078 |
| 1 | A | AB000895 | 0.000000 |
| 1 | A | AB000896 | 0.735730 |
| 1 | A | AB000897 | 0.412747 |
| 1 | A | AB001106 | 0.284690 |
| 1 | A | AB001325 | 0.000000 |
| 1 | A | AB002314 | 0.319384 |
| 1 | A | AB002315 | 0.014804 |
| 1 | A | AB002318 | 0.000152 |
| 1 | A | AB002332 | 0.010357 |
| 1 | A | AB002356 | 0.249101 |
| 1 | A | AB002365 | 0.424078 |
| 1 | A | AB002366 | 0.557659 |
| 1 | A | AB002380 | 0.063612 |
| 1 | A | AB002382 | 0.003653 |
| 1 | A | AB002409 | 0.356706 |
| 1 | A | AB002533 | 0.000002 |
| 1 | A | AB002559 | 0.000103 |

The column headings in Table 4 are as follows:
CHIP: Identifies the chip design being analyzed. In this case, "1" refers to the Human 6.8 k chip.
STRAND: "A"=anti-sense or "S"=sense; indicating the strand being interrogated.
PROBESET: Gene Accession Number or descriptor.
P-TIME: P-value for change over time.
Consider the following two entries from Table 4:

| CHIP | STRAND | PROBESET | P-TIME |
|---|---|---|---|
| 1 | A | AB000895 | 0.000000 |
| 1 | A | AB000896 | 0.735730 |

The expression level of the gene AB000895 changes significantly over time while AB000896 shows no significant temporal change.

In Table 4, the columns {CHIP, STRAND, PROBESET} form a compound unique index that identifies each gene in the analysis. Thus, queries can be formulated to select a subset of genes that meet specific criteria based on within-chip analysis results and the analysis of variance results. In this example, the goal was to identify all genes meeting the following criteria:
1. Significantly change over time (P-TIME<0.0000001)
2. Are present at one or more time points (PNULL[0] <0.0000001 or PNULL[4]<0.0000001 or PNULL[24] <0.0000001 or PNULL[144]<0.0000001) or PNULL [288]<0.0000001), where PNULL[t] is the P-value for the within-chip comparison with the "Null Set" at time t.
3. Their change over time spans a minimal fold-change (Max (AVGI)/Min (AVGI)>3), where Max and Min are taken over the five time points.
This query selected 134 genes.

Figure 8:
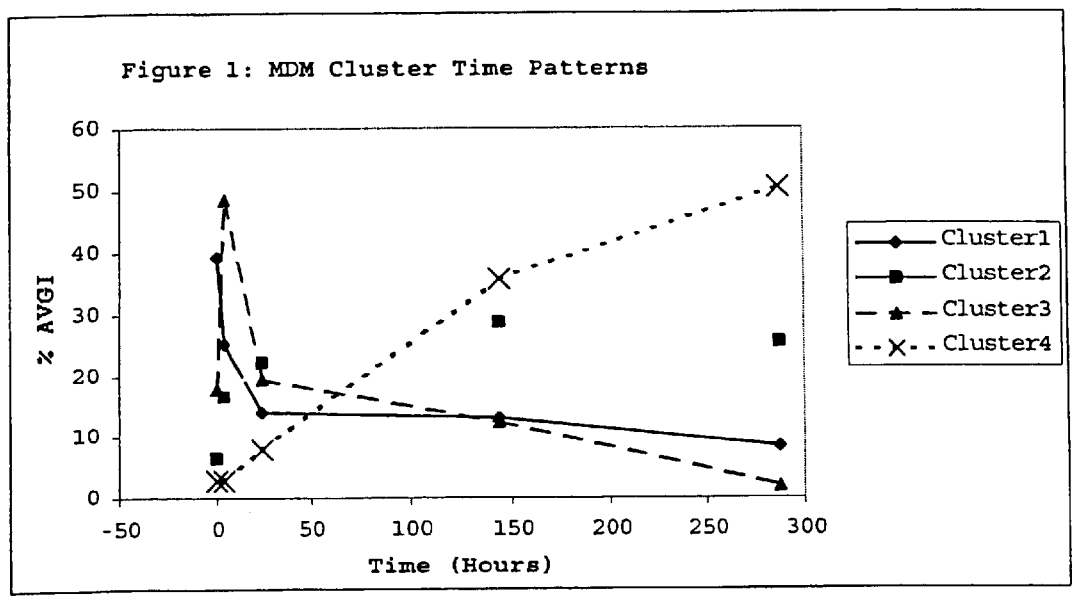
FIG. 8 is a graph depicting the change in intensity over time for four cluster of genes identified in a hybridization experiment analyzed according to the invention.

These genes were then clustered using the five time points AVGI (expressed as percentage of the sum of the five time points) according to known clustering techniques such as those described in J. A. Haligan, *Clustering Algorithms* (John Wiley & Sons, Inc. 1975) and Ward, J. H., "Hierarchical Grouping to Optimize an Objective Function," *J. Am. Statistical Assoc.* 58, pp. 236–244 (1963). The 134 genes fell into four clusters: 49 genes in Cluster1; 42 genes in Cluster2; 22 genes in Cluster3 and 21 genes in Cluster4. Observed time trajectories for each of the four clusters are shown in FIG. 8.

Cluster1 contains genes that have a decelerated decrease in their expression levels over time, the expression level drops early and then levels off. Cluster2 is a mirror image of Cluster1; it contains genes that have a decelerated increase in their expression levels over time, the expression level increases fast early and then levels off. Cluster3 contains genes that peak at 4 hours and then decrease slowly. Cluster4 contains genes that show linear increase over time.

Implementation

The invention can be implemented in digital electronic circuitry, or in computer hardware, firmware, software, or in combinations of them. Apparatus of the invention can be implemented in a computer program product tangibly embodied in a machine-readable storage device for execution by a programmable processor; and method steps of the invention can be performed by a programmable processor executing a program of instructions to perform functions of the invention by operating on input data and generating output. The invention can be implemented advantageously in one or more computer programs that are executable on a programmable system including at least one programmable processor coupled to receive data and instructions from, and to transmit data and instructions to, a data storage system, at least one input device, and at least one output device. Each computer program can be implemented in a high-level procedural or object-oriented programming language, or in assembly or machine language if desired; and in any case, the language can be a compiled or interpreted language. Suitable processors include, by way of example, both general and special purpose microprocessors. Generally, a processor will receive instructions and data from a read-only memory and/or a random access memory. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM disks. Data can also be temporarily stored in volatile memory. Any of the foregoing can be supplemented by, or incorporated in, ASICs (application-specific integrated circuits).

To provide for interaction with a user, the invention can be implemented on a computer system having a display device such as a monitor or LCD screen for displaying information to the user and a keyboard and a pointing device such as a mouse or a trackball by which the user can provide input to the computer system. The computer system can be programmed to provide a graphical user interface through which computer programs interact with users.

The invention has been described in terms of particular embodiments. Other embodiments are within the scope of the following claims.

What is claimed is:

1. A database on a computer readable medium comprising:
   a set of experimental values derived from an experiment, the experiment comprising the reaction of a target sample with a biomolecular array, the array comprising one or more probe sets, each probe set comprising a collection of one or more probes, each value in the set of experimental values corresponding to the interaction of the target sample with one of the probes; and
   a set of one or more probability values for at least one probe set including a first probability value indicating the probability that a molecular species complementary to the probe set is not present in the target sample, the first probability value being generated by comparing the values for the probes in the probe set with a value for the calibration set, the calibration set comprising a null set of probes that are substantially absent in the target sample.

2. The database of claim 1, further comprising:
   one or more second probability values for the at least one probe set, the second probability values indicating the probability that the molecular species complementary to the probe set is present at a level greater than or less than a reference concentration.

3. The database of claim 2, wherein:
   the one or more second probability values are generated by comparing the values for the probes in the probe set with values for the calibration set.

4. The database of claim 3, further comprising:
   a normalized value for at least one probe set, the normalized value being derived from an interpolated value on a curve defined by the values for the calibration set.

5. The database of claim 4, wherein the normalized value is a gamma normalized value.

6. The database of claim 4, wherein the normalized value is a principal component score.

7. The database of claim 4, wherein the normalized value is a cumulative distribution function score.

8. A method of analyzing an experiment, the experiment comprising the reaction of a target sample with a biomolecular array, the array comprising one or more probe sets, each probe set comprising a collection of one or more probes, the method comprising:
   receiving a set of values, each value corresponding to the interaction of the target sample with one of the probes; and
   using the set of values to generate for at least one probe set a first probability value indicating the probability that a molecular species complementary to the probe set is not present in the target sample by comparing the set of values for the probes in the probe set with one or more values for probes in a calibration set, the calibration set comprising a null set of probes expected to be substantially absent in the target sample.

9. The method of claim 8, further comprising:
   using the set of values to generate one or more second probability values for the at least one probe set, the second probability values indicating the probability that the molecular species complementary to the probe set is present at a level greater than or less than a reference concentration by comparing the set of values for probes in the probe set with one or more values for probes in the calibration set.

10. The method of claim 9, further comprising:
    outputting an output file comprising the first and second probability values for at least one probe set.

11. The method of claim 8, wherein comparing the values for the probes in the probe set with the value for the calibration set comprises using a likelihood ratio algorithm.

12. The method of claim 8, wherein comparing the values for the probes in the probe set with the value for the calibration set comprises using an order statistics algorithm.

13. The method of claim 8, further comprising:
    using the set of values to generate for at least one probe set one or more second probability values indicating the probability that the molecular species complementary to the probe set is present at a level greater than or less than a reference concentration.

14. The method of claim 13, further comprising:
    using the first and second probability values to generate a normalized value for at least one probe set.

15. The method of claim 9, wherein using the first and second probability values to generate a normalized value comprises generating an interpolated value on a curve defined by the values for the calibration set.

16. The method of claim 9, wherein the calibration set comprises a set of spiked probes.

17. The method of claim 9, wherein the calibration set comprises one or more probes derived from a set of endogenous housekeeping genes.

18. The method of claim 15, further comprising:
    outputting an output file comprising the normalized value for at least one probe set.

19. The method of claim 18, wherein the normalized value for the at least one probe set comprises a gamma-normalized value for the at least one probe set.

20. The method of claim 18, wherein the normalized value for the at least one probe set comprises a principal component score for the at least one probe set.

21. The method of claim 18, wherein the normalized value for the at least probe set comprises a cumulative distribution function score for the at least probe set.

22. A computer program on a computer-readable medium for analyzing an experiment, the experiment comprising the reaction of a target sample with a biomolecular array, the array comprising one or more probe sets, each probe set comprising a collection of one or more probes, the program comprising instructions operable to cause a programmable processor to:
    receive a set of values, each value corresponding to the interaction of the target sample with one of the probes; and
    use the set of values to generate for at least one probe set a first probability value indicating the probability that a molecular species complementary to the probe set is not present in the target sample by comparing the set of values for the probes in the probe set with one or more values for probes in a calibration set, the calibration set comprising a null set of probes expected to be substantially absent in the target sample.

23. The computer program of claim 22, further comprising instructions operable to cause the programmable processor to:
    use the set of values to generate one or more second probability values for the at least one probe set, the second probability values indicating the probability that the molecular species complementary to the probe set is present at a level greater than or less than a reference concentration by comparing the set of values for probes in the probe set with one or more values for probes in the calibration set.

24. The computer program of claim 9, further comprising instructions operable to cause the programmable processor to:

output an output file comprising the first and second probability values for at least one probe set.

25. The computer program of claim 22, wherein the instructions operable to compare the values for the probes in the probe set with the value for the calibration set comprise instructions to use a likelihood ratio algorithm.

26. The computer program of claim 22, wherein the instructions operable to compare the values for the probes in the probe set with the value for the calibration set comprise instructions to use an order statistics algorithm.

27. The computer program of claim 22, further comprising instructions operable to cause a programmable processor to:

use the set of values to generate for at least one probe set one or more second probability values indicating the probability that the molecular species complementary to the probe set is present at a level greater than or less than a reference concentration.

28. The computer program of claim 27, further comprising instructions operable to cause a programmable processor to:

use the first and second probability values to generate a normalized value for at least one probe set.

29. The computer program of claim 23, wherein the instructions operable to use the first and second probability values to generate a normalized value comprise instructions operable to generate an interpolated value on a curve defined by the values for the calibration set.

30. The computer program of claim 23, wherein the calibration set comprises a set of spiked probes.

31. The computer program of claim 23, wherein the calibration set comprises one or more probes derived from a set of endogenous housekeeping genes.

32. The computer program of claim 29, further comprising instructions operable to cause a programmable processor to:

output an output file comprising the normalized value for at least one probe set.

33. The computer program of claim 32, wherein the normalized value for the at least one probe set comprises a gamma-normalized value for the at least one probe set.

34. The computer program of claim 32, wherein the normalized value for the at least one probe set comprises a principal component score for the at least one probe set.

35. The computer program of claim 32, wherein the normalized value for the at least one probe set comprises a cumulative distribution function score for the at least one probe set.

36. A method of analyzing an experiment, the experiment comprising the reaction of a target sample with a biomolecular array, the array comprising one or more probe sets, each probe set comprising a collection of one or more probes, the method comprising:

receiving a set of values, each value corresponding to the interaction of the target sample with one of the probes; and using the set of values to generate for at least one probe set a first probability value indicating the probability that a molecular species complementary to the probe set is not present in the target sample and one or more second probability values indicating the probability that the molecular species complementary to the probe set is present at a level greater than or less than a reference concentration by comparing the set of values for the probes in the probe set with a plurality of values for probes in a calibration set, the calibration set comprising a null set of probes expected to be substantially absent in the target sample and one or more spiked probes and/or probes derived from a set of endogenous housekeeping genes.

* * * * *